(12) United States Patent
Choi (10) Patent No.: US 12,287,317 B2
(45) Date of Patent: Apr. 29, 2025

(54) WATER SAMPLER

(71) Applicant: Jongyoul Choi, Seoul (KR)

(72) Inventor: Jongyoul Choi, Seoul (KR)

( * ) Notice: Subject to any disclaimer, the term of this patent is extended or adjusted under 35 U.S.C. 154(b) by 328 days.

(21) Appl. No.: 18/016,986

(22) PCT Filed: Jul. 24, 2020

(86) PCT No.: PCT/KR2020/009797
§ 371 (c)(1),
(2) Date: Jan. 19, 2023

(87) PCT Pub. No.: WO2022/019363
PCT Pub. Date: Jan. 27, 2022

(65) Prior Publication Data
US 2023/0280326 A1 Sep. 7, 2023

(51) Int. Cl.
| | |
|---|---|
| G01K 1/14 | (2021.01) |
| G01N 1/16 | (2006.01) |
| G01N 1/20 | (2006.01) |
| G01N 33/18 | (2006.01) |

(52) U.S. Cl.
CPC ............ *G01N 33/1886* (2013.01); *G01K 1/14* (2013.01); *G01N 1/16* (2013.01); *G01N 1/20* (2013.01)

(58) Field of Classification Search
CPC .. G01K 1/14; G01N 1/16; G01N 1/20; G01N 33/1886
See application file for complete search history.

(56) References Cited

FOREIGN PATENT DOCUMENTS

| | | | |
|---|---|---|---|
| CN | 102680277 B | | 10/2014 |
| CN | 105527129 A | * | 4/2016 |
| JP | H10197419 A | | 7/1998 |
| JP | 2010190625 A | | 9/2010 |
| KR | 200118410 Y1 | | 8/1998 |
| KR | 100896979 B1 | | 5/2009 |
| KR | 20120014310 A | | 2/2012 |
| KR | 20150034487 A | * | 4/2015 |
| KR | 20200109458 A | | 9/2020 |

OTHER PUBLICATIONS

International search report of PCT/KR2020/009797, Apr. 13, 2021, English translation.

* cited by examiner

*Primary Examiner* — Jamel E Williams
(74) *Attorney, Agent, or Firm* — STIP Law Group, LLC (57) ABSTRACT

The present disclosure relates to a water sampler comprising: a container which is open at the top thereof; a first stopper which comprises a first upper plate and a first wall and has a drain outlet; a second stopper which comprises a second upper plate and a second wall; an elastic member which is disposed between the first upper plate and the second upper plate; a weight which is disposed at the bottom of the container; and a fixing member to which a second rope is connected, whereby water sampling and temperature measurement can be easily and accurately performed at a desired water depth without limitations on measurement items.

5 Claims, 7 Drawing Sheets

WATER SAMPLER

CROSS-REFERENCE TO RELATED APPLICATIONS

This application is the U.S. National Phase under 35 U.S.C. § 371 of International Application No. PCT/KR2020/009797 filed on Jul. 24, 2020, the entire disclosures of which are incorporated by reference into the present application.

TECHNICAL FIELD

The present disclosure relates to a water sampler, and more particular, to a water sampler which may move down to a desired depth of water without floating by buoyancy and may easily switch an opening or a closing of a container through manpower, thereby easily and accurately performing water sampling and temperature measurement without limitations on measurement items at the desired depth of water without additional power.

BACKGROUND ART

The water quality test is meant to investigate physico-chemical properties of water or chemical components or microorganisms contained in water, and is performed for a variety of purposes, including when selecting sources of water supply, when inspecting and monitoring the contamination or purification of water sources, when inspecting checking the acceptance of tap water for a water quality standard, when measuring an environmental pollution level of a river, a stream, or the sea, and when checking a contamination level of industrial water or sewerage.

In order to conduct such a water quality test, samples, that is, water, has to be collected from a river or the sea, and a water sampler is used to collect such water. Currently, various types of water samplers have been developed and used.

Among these water samplers, there is a water sampler with a structure that operates only with manpower without using additional power. The conventional manual water sampler has a structure in which a stopper is usually provided at an inlet of a container of the water sampler and is connected to a string so that when the water sampler reaches a certain depth of water, the string is pulled to open the stopped to collect the sample.

However, since the conventional manual water sampler has an accommodation space for holding the sample inside, it is difficult to collect deep water by buoyancy, and when the string connected to the stopper is pulled to collect the sample, the whole water sampler cannot withstand a force of pulling the string and moves up, which may make it difficult for a user to accurately collect the water at a desired depth of water.

In addition, the characteristics of water may vary depending on positions where water is collected. Once the stopped is opened, since the container remains open until the water sampler is raised above water, the water collection may not be performed at the desired depth of water, and water may be mixed and collected at various depths.

In addition, a material of the container of the water sampler can needs to be classified according to characteristics of the sample to be collected and a desired evaluation method. Since the conventional water sampler has a single body, it is inconvenient to conduct a water quality test by replacing a water sampler with a water sample having a different material depending on the characteristics and evaluation method of the sample.

In addition, the conventional water sampler, it may be difficult to immediately measure an exact temperature at a water-collecting place.

PRIOR ART DOCUMENT

Patent Document

Korean Patent No. 10-0896979
Korean Unexamined Patent Application Publication No. 10-2012-0014310

DISCLOSURE

Technical Problem

The present disclosure has been derived to solve the aforementioned problems of the prior art, and objects of the present disclosure provide a water sampler that can be disposed at a desired depth without floating due to buoyancy and can easily switch an opening or closing of a container by manpower, thereby accurately performing water sampling at a desired depth of water without additional power.

Objects of the present disclosure also provide a water sampler which can selectively collect a sample by dividing an accommodation portion into a plastic container and a glass container according to the characteristics of the sample.

Objects of the present disclosure also provide a water sampler which can provide a user with a sample temperature in real time at the site such that the user can take the necessary measures quickly or immediately measure the characteristics of the sample at the site when the characteristics of samples vary with temperature.

Technical Solution

According to one aspect of the present disclosure to achieve the objects, a water sampler includes: a container of which an upper portion is opened; a first stopper including a first upper plate having a through hole formed therein, and a first wall portion which extends downwardly from an edge of the first upper plate and of which an upper end is coupled to an outer surface of a bottleneck of the container, wherein at least one sample inlet is formed on a side surface of the first wall portion; a second stopper including a second upper plate having a handle portion long protruding upwardly to be exposed through the through hole of the first stopper and connected to a first rope, and a second wall portion extending downwardly from an edge of the second upper plate, wherein the second stopper is installed to move up and down in the first stopper such that the second wall portion selectively opens or closes an open upper portion of the container; an elastic member installed between the first upper plate and the second upper plate; a weight installed in a lower end of the container; and a fixing member which fixes the weight to the container and to which a second rope is connected.

According to the preferred embodiment, the container may further include a transparent glass bottle which is made of transparent plastic and is open at the top thereof by including a bottom plate and a wall surface and a first accommodation portion is provided inside, and in which the first stopper is coupled to an upper end of the wall surface, and the transparent glass bottle may be installed on the bottom plate of the container to be spaced apart from the wall surface of the container such that a second accommodation portion is provided inside, and an upper end of the transparent glass bottle may be disposed higher than the bottleneck of the container such that a sample collected in the second accommodation portion is not mixed with a sample collected in the first accommodation portion when the sample is drained.

According to the preferred embodiment, a mounting protrusion may be provided on the bottom plate of the container such that an upper end of the glass bottle may be inserted and fixed.

According to the preferred embodiment, two or more holders may be installed around the glass bottle to be spaced apart in a vertical direction, the holder may include a band-shaped holder body surrounding a circumference of the glass bottle and a ring portion protruding from the holder body, and the water sampler may further include a thermometer supported by the ring portion disposed vertically and installed in the first accommodating portion provided between the container and the glass bottle.

According to the preferred embodiment, the holder may be made of a thermally conductive metal.

Advantageous Effect

According to an embodiment of the present disclosure, a water sampler can be prevented from floating due to buoyancy using a weight and be disposed in a desired depth of water, and an opening and closing of a container can be easily switched by manpower such that a first rope of a second stopper is pulled to open a container, or elasticity of an elastic member is used to automatically close the container, thereby making it possible to accurately collect water in a state in which the water is blocked from external samples or air at a desired depth of water without additional power.

In addition, since an accommodation portion is divided into two spaces by a plastic container and a glass bottle installed inside the container, one water sampler can selectively collect samples by distinguishing the plastic container and the glass container according to the characteristics of the sample and a desired evaluation method.

In addition, since the temperature of the sample can be provided in real time at the site as necessary by using a thermometer installed in a first accommodating portion, when there are samples whose characteristics vary with temperature, necessary measures may be taken immediately and promptly at the site, or the characteristics of the sample may be measured immediately at the site.

MODE FOR DISCLOSURE

Hereinafter, a water sampler according to various embodiments of the present disclosure will be described with reference to the attached drawings.

The water sampler according to an embodiment of the present disclosure may collect river water, lake water, seawater, etc. only with manpower without power such as electricity or pneumatic pressure.

Figure 1:
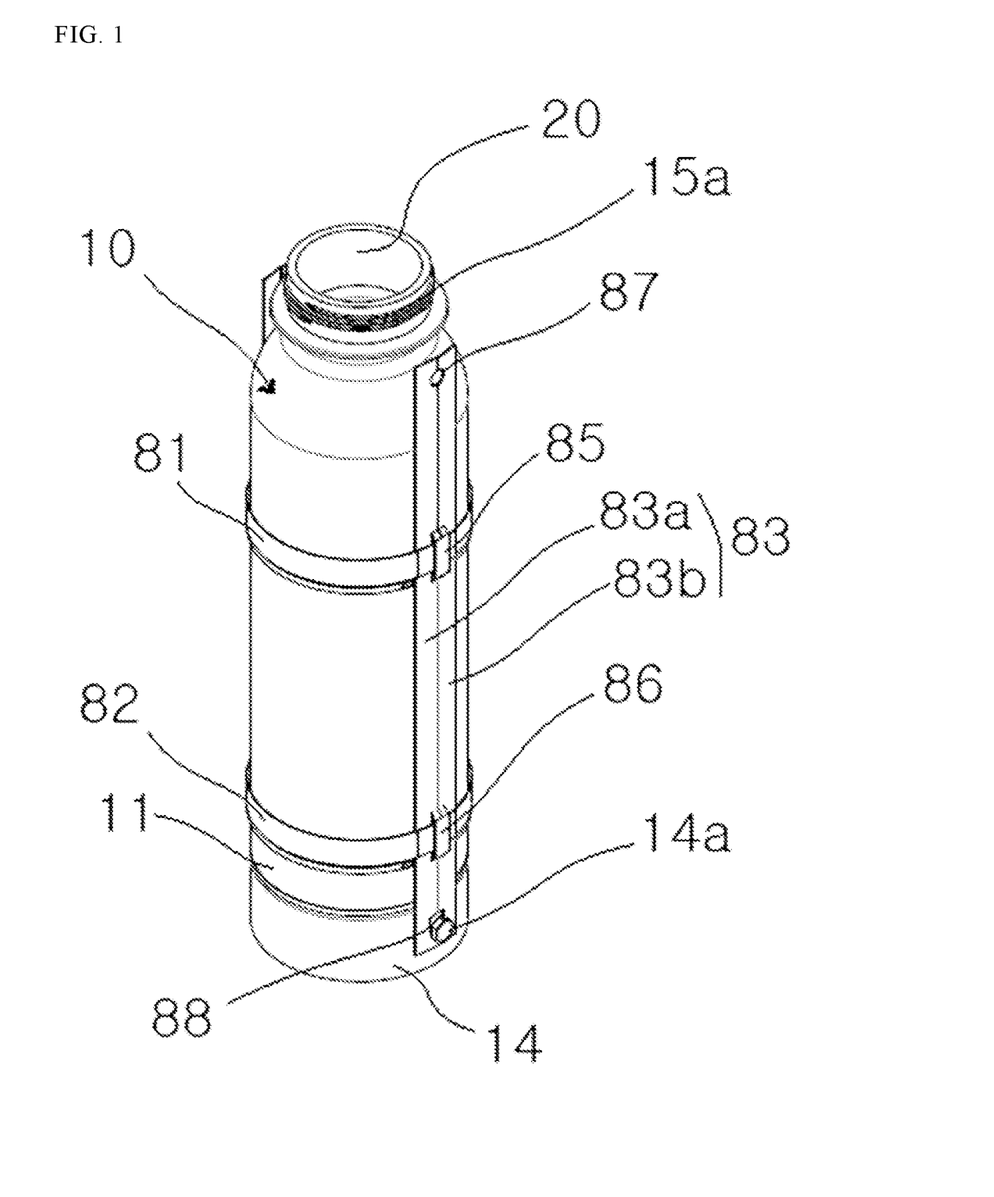
FIG. 1 is a perspective view illustrating a state in which a container, a glass bottle, a weight, and a fixing member are coupled to each other in a water sampler according to an embodiment of the present disclosure.
Figure 2:
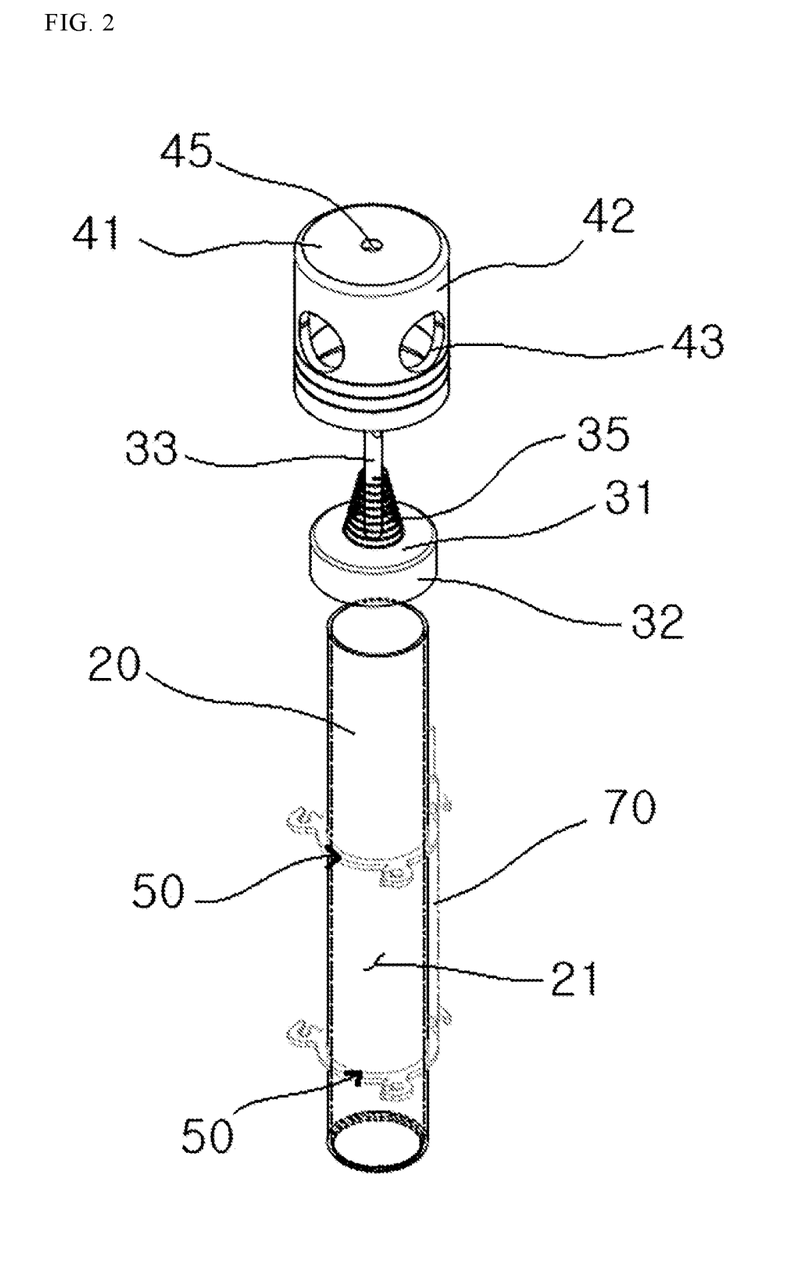
FIG. 2 is an exploded perspective view illustrating a coupling structure of a glass bottle, a first stopper, and a second stopper in the water sampler according to an embodiment of the present disclosure.
Figure 3:
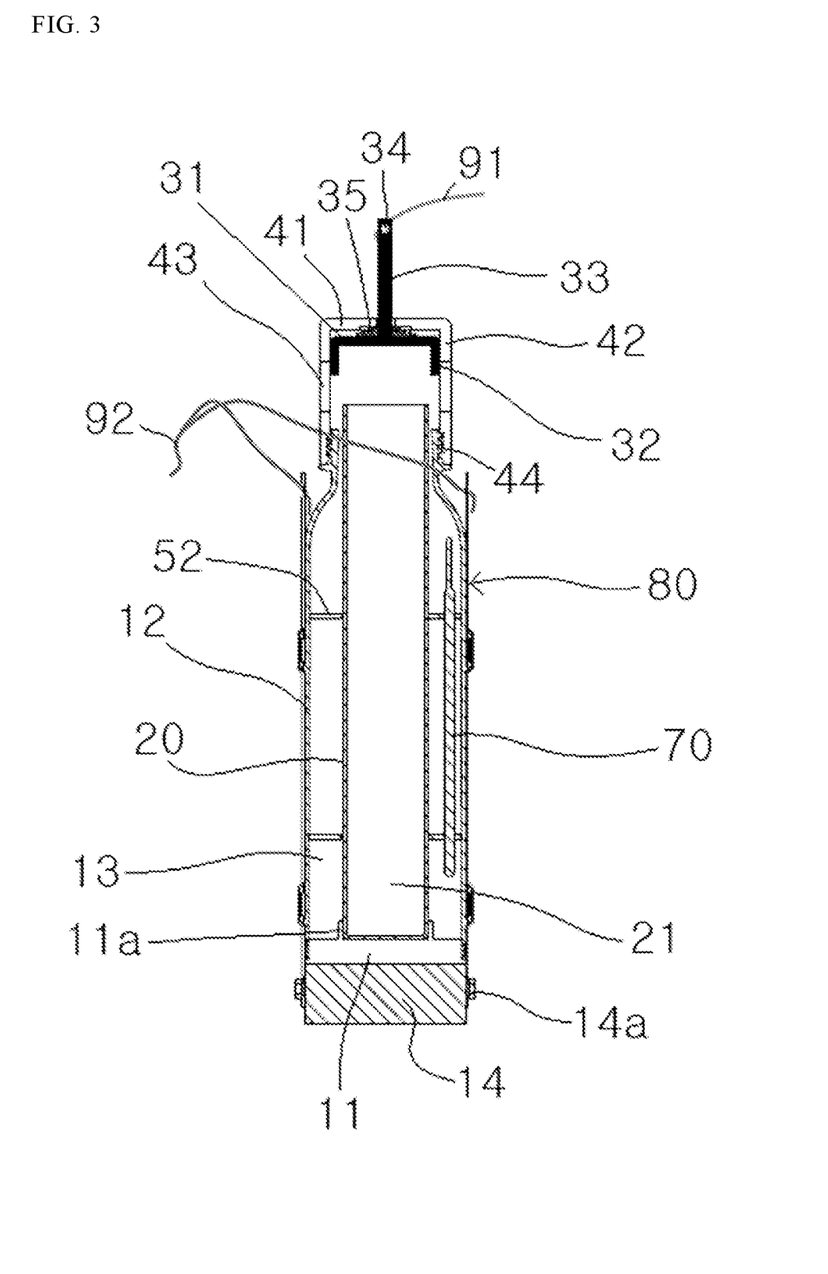
FIG. 3 is a cross-sectional view illustrating a state in which a container and a glass bottle are opened in the water sampler according to an embodiment of the present disclosure.
Figure 4:
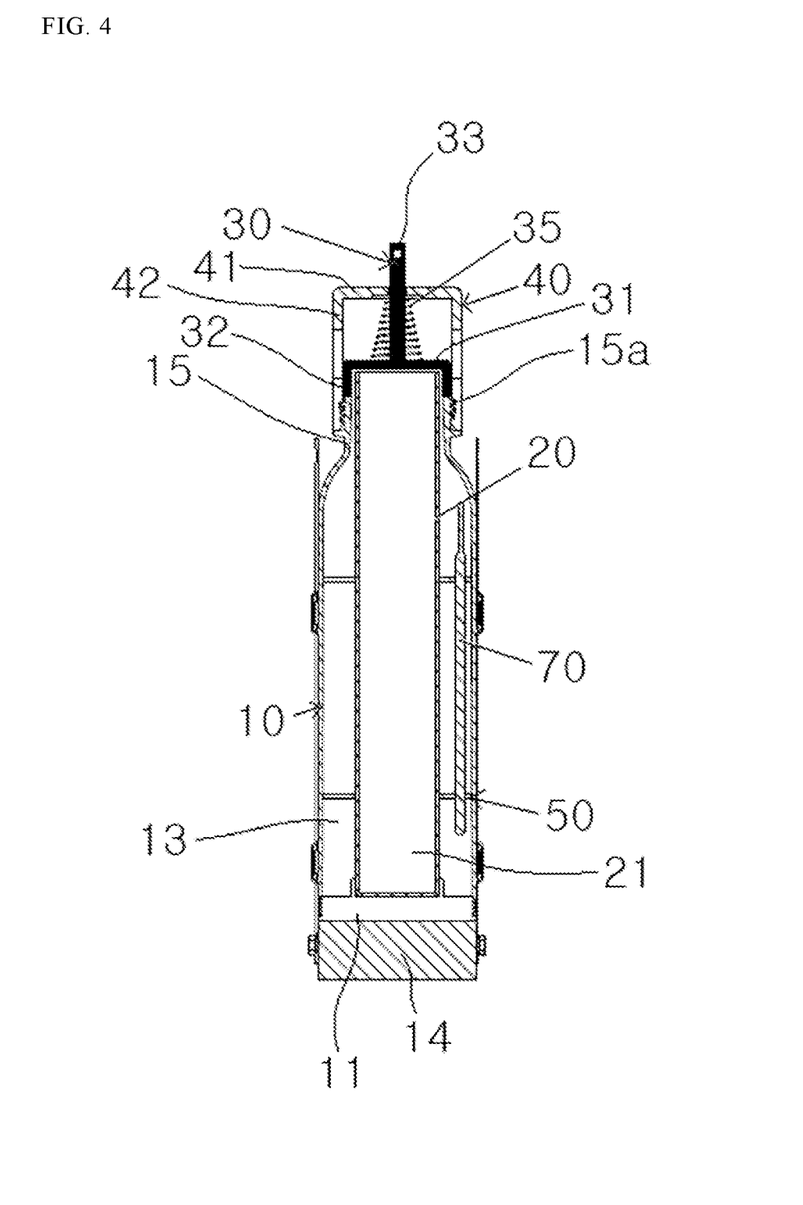
FIG. 4 is a cross-sectional view illustrating a state in which the container and the glass bottle are closed in the water sampler according to an embodiment of the present disclosure.

FIG. 1 is a perspective view illustrating a state in which a container, a glass bottle, a weight, and a fixing member are coupled to each other in a water sampler according to an embodiment of the present disclosure, FIG. 2 is an exploded perspective view illustrating a coupling structure of a glass bottle, a first stopper, and a second stopper in the water sampler according to an embodiment of the present disclosure, FIG. 3 is a cross-sectional view illustrating a state in which a container and a glass bottle are opened in the water sampler according to an embodiment of the present disclosure, and FIG. 4 is a cross-sectional view illustrating a state in which the container and the glass bottle are closed in the water sampler according to an embodiment of the present disclosure.

Referring to FIGS. 1 to 4, the water sampler according to one embodiment of the present disclosure includes a container 10, a first stopper 40, a second stopper 30, an elastic member 35, a weight 14, and a fixing member 80.

The container 10 may include a bottom plate 11 and a wall surface 12 such that an upper portion thereof is opened, and has a first accommodation portion 13 inside. In this case, the container 10 may have a screw thread 15a formed such that the first stopper 40 may be coupled to an outer surface of a bottleneck 15 provided in the upper end of the wall surface 12. In addition, the container 10 has a certain level of durability and may be made of transparent plastic material such that a content collected in the first accommodation portion 13 may be easily checked with a user's eyes.

In addition, the bottom plate 11 of the container 10 may be provided with a mounting protrusion 11a having a size corresponding to the circumference of the glass bottle such that a lower end of a glass bottle described below can be firmly inserted and fixed without shaking.

In addition, the water sampler of the present disclosure may further include a glass bottle 20 made of glass having a transparent material. The glass bottle 20 is in the form of a bottle in which only an upper portion thereof is opened, and may be installed on the bottom plate 11 of the container 10 to get spaced apart from the wall surface 12 of the container 10 such that a second accommodation portion 21 is provided inside.

When the transparent glass bottle 20 is embedded in the container 10, water collected at once may be used for two different types of tests. This will be described in detail below.

In addition, an upper end of the glass bottle 20 may be disposed higher than the bottleneck 15 of the container 10. If the upper of the glass bottle 20 is lower than the bottleneck 15 of the container 10, the sample accommodated in the first accommodation portion 13 and the sample accommodated in the second accommodation portion 21 may be mixed during storage, and in the process of tilting and re-erecting the water sampler during drainage, some of the samples contained in the second accommodation portion 21 are mixed into the first accommodation portion 13. When the sample accommodated in the first accommodation portion 13 and the sample accommodated in the second accommodation portion 21 are mixed with each other, it may be difficult to measure the exact values of each sample when measuring the characteristics of the samples. In the embodiment, the upper end of the glass bottle 20 may be formed higher than the bottleneck of the container 10, thereby preventing such a problem and accurately measuring each of the samples accommodated in the first accommodation portion 10 and the second accommodation portion 20.

The first stopper 40 includes a first upper plate 41 having a through hole 45 formed in the center thereof and a first wall 42. In this case, the through-hole 45 may be further provided with a packing as necessary.

The first wall 42 is a portion extending downwardly from an edge of the first upper plate 41, and a lower end thereof is coupled to an outer surface of the bottleneck 15 of the container 10, and in this case, a screw thread 44 corresponding to the screw thread 15a formed in the bottleneck 15 of the container 10 may be formed on an inner surface of a lower end of the first wall 42.

In addition, at least one sample inlet 43 may be formed on a side surface of the first wall 42. In the embodiment of the present disclosure, a total of four sample inlets are formed in the first wall 42 of the first stopper 40 in four directions, that is, front and rear, and left and right, so as to facilitate introduction of the sample, but the present disclosure is not limited thereto, and one to three or five sample inlets may be formed as necessary.

The second stopper 30 includes a second upper plate 31 and a second wall 32.

The second upper plate 31 may have a rod-shaped handle 33 that protrudes upward to be exposed through the through hole 45 of the first stopper 40, and a coupling hole 34 may be formed in an end of the handle 33 such that a first rope 91 may be connected to the coupling hole 34.

The second wall part 32 is a portion extending downwardly from an edge of the second upper plate 31, and serves to selectively open or close the opened upper part of the container 10, and accordingly, the second wall 32 may be formed to have a diameter corresponding to the bottleneck 15 of the container 10. The second stopper 30 is installed to be movable vertically in the first stopper 40, and when the second stopper 30 descends, the second wall 32 is in close contact with the upper portion of the container 10 to close the opened upper portion of the container 10, and when the first rope 91 is pulled to increase the second stopper 30, the second wall 32 is spaced apart from the upper portion of the container 10 to open the upper portion of the container 10. In this case, an upper portion of the glass bottle 20 may be selectively opened or closed according to the ascending and descending of the second stopper 30.

The elastic member 35 is installed between the first upper plate 41 and the second upper plate 31, and may be preferably formed of a coil spring in which an upper end thereof is fixed to an inner surface of the first upper plate 41 and a lower end thereof is fixed to an outer surface of the second upper plate 31.

The elastic member 35 elastically grabs the second upper plate 31 of the second stopper 30 so that the second stopper 30 descends in the first stopper 40 and the second wall 32 of the second stopper 30 closes the upper portion of the container 10, and when the first rope 91 connected to the handle 33 of the second stopper 30 is pulled upward to ascend the second stopper 30 upward, as the second wall 32 is spaced apart from the upper end of the container 10, the open upper portion of the container 10 is opened.

Then, when the first rope 91 of the pulled handle 33 is released, the second upper plate 31 is lowered and pushed down by the elasticity of the elastic member 35 and returns to an original position thereof to close the opened upper portion of the container 10 and the upper portion of the glass bottle 20 again.

The weight 14 serves to drop the water sampler to a desired depth of water and prevent the water sampler from unexpectedly ascending during the collection of the sample, and may be installed in close contact with a lower surface of the bottom plate 11 of the container 10.

In this case, the weight 14 may be appropriately adjusted to provide an enough load to open only the second stopper 30 so as to prevent the container 10 as well as the second stopper 30 from being pulling up together when pulling the first rope 91 of the second stopper 30.

Two coupling protrusions 14a protrude around the weight 14 so as to couple a support of the fixing member described below, and the coupling protrusions 14a may be formed one by one at a position where they face each other in left and right directions. In addition, since the weight 14 of the embodiment is not integrated with the container and has an easily detachable structure, it is possible to easily perform tasks such as replacement of the weight as necessary.

The fixing member 80 serves to fix the weight 14 to the container 10, and the second rope 92 may be connected to the fixing member 80.

In detail, the fixing member 80 may include two upper and lower fixing holders, that is, first and second fixing holders 81 and 82, and two left and right supports elongated in the vertical direction, that is, first and second supports. The first and second fixing holders 81 and 82 are formed in a band shape to surround the circumference of the container 10, and are vertically spaced from each other around an outer circumference of the container 10. The first and second supports are disposed one by one at a position where they face each other in the left and right directions of the container 10. Hereinafter, the first support 83 is described, but the second support has the same structure as the first support 83, and the following description is considered to include a description of the second support.

The first support 83 includes first and second vertical members 83a and 83b disposed to face each other on the left and right sides. In this case, the first and second vertical members 83a and 83b have semicircular grooves formed at both upper and lower ends such that they face each other, and when the first and second vertical members 83a and 83b are in close contact with each other on the left and right sides, coupling hole 87 and 88 are provided at upper and lower portions of the first support 83, respectively. In addition, one of the first and second vertical members 83a and 83b is provided with two fixing pieces 85 and 86 having through holes in a horizontal direction, which are spaced apart from each other in the vertical direction.

Accordingly, the first and second vertical members 83a and 83b are disposed to face both sides of the container 10 while being in close contact with each other on the left and right sides such that a semicircular groove formed on the bottom is inserted into the coupling protrusion 14a of the weight 14, and when each of the two fixing holders 81 and 82 is installed on an outer surface of the container 10 to pass through the through holes of the upper and lower fixing pieces 85 and 86, respectively, it is possible to stably prevent the weight 14 from being separated from the bottom plate 11 of the container 10. Meanwhile, a second rope 92 may be connected to upper holes of the first and second supports. The second rope 92 may be used to refloat the water sampler to the ground.

Meanwhile, the water sampler of the present disclosure has a structure in which the glass bottle 20 is installed inside the plastic container 10 as described above.

Accordingly, when the second stopper 30 is opened, water flows into the water sampler through the sample inlet 43 of the first stopper 40, and in this case, some of the water may flow into the first accommodation portion 13 provided inside the container 10, and the other water may flow into the second accommodation portion 21 provided inside the glass bottle 20.

Therefore, the water collected at once by one water sampler may be divided and used in two types of tests having different storage standards. For example, "Sampling for Acute Toxicity Test of Water Flea" stipulates that highly toxic plastic containers such as polyethylene should not be used to avoid affecting water fleas when drinking water, and only glass containers should be used. In other words, since the sample accommodated in the first accommodation portion 13 covered with the plastic container 10 is not suitable for a sample for confirming the ecological toxicity of water fleas, the sample accommodated in the first accommodation portion 13 may be used as a BOD-related sample. In addition, the sample accommodated in the second accommodation portion 21 covered with the glass bottle 20 that is not ecotoxic can be used for a 'water flea acute toxicity test.'

According to the Ministry of Environment Notice (No. 2004-188) on the water pollution process test method, for general measurement items such as temperature, hydrogen ion concentration, and the like, both plastic and glass containers may be used as sample preservation containers, but only glass containers are allowed for special measurement items such as normal hexane extraction, phenol, organic phosphorus, polychlorinated biphenyl (PCB), and volatile lower hydrocarbon concentrations, and only plastic containers are allowed for special measurement items such as fluorine concentration.

Since the water sampler according to the present disclosure is provided by separating the first accommodation portion 13 for the plastic container from the second accommodation portion 21 for the glass bottle, various items may be simultaneously measured with only one collection for the special measurement item in addition to general measurement items.

In another embodiment, in order to properly measure the characteristics of the collected sample, it is necessary to keep the temperature within a specific range in some cases, and in order to clearly manage the temperature of the sample, the temperature of the sample needs to be measured easily and accurately whenever necessary.

Figure 5:
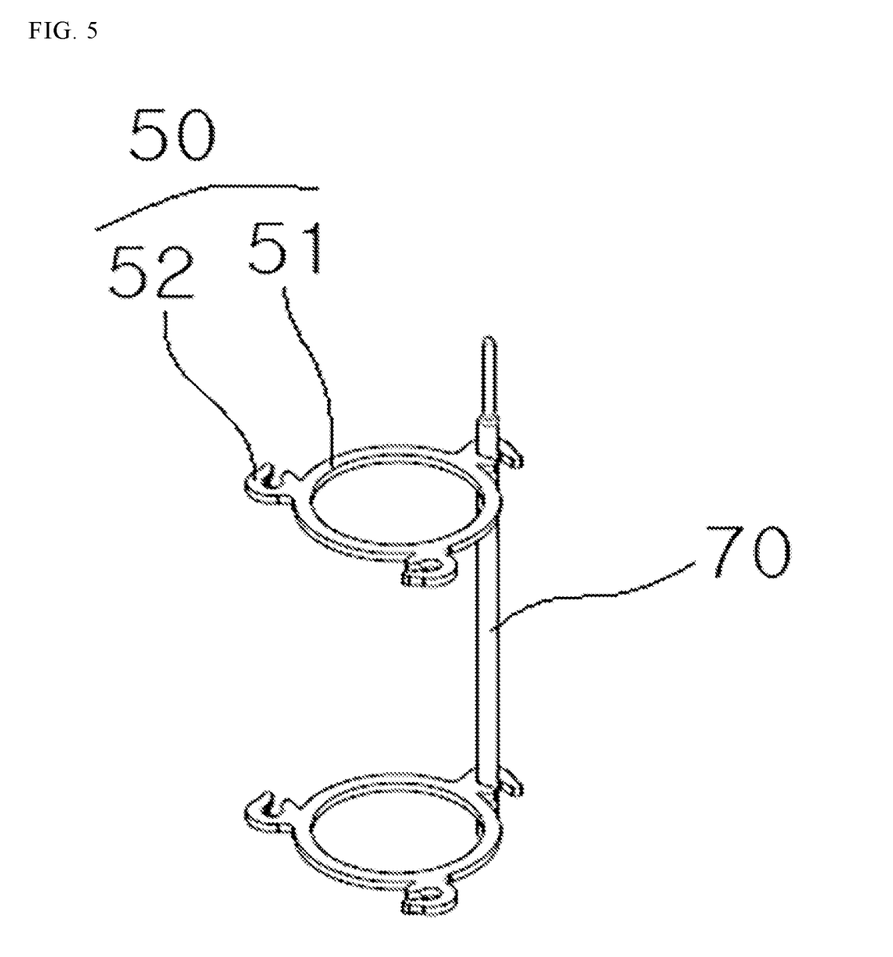
FIG. 5 is a perspective view illustrating a state in which a holder and a thermometer are coupled in the water sampler according to an embodiment of the present disclosure.
Figure 6:
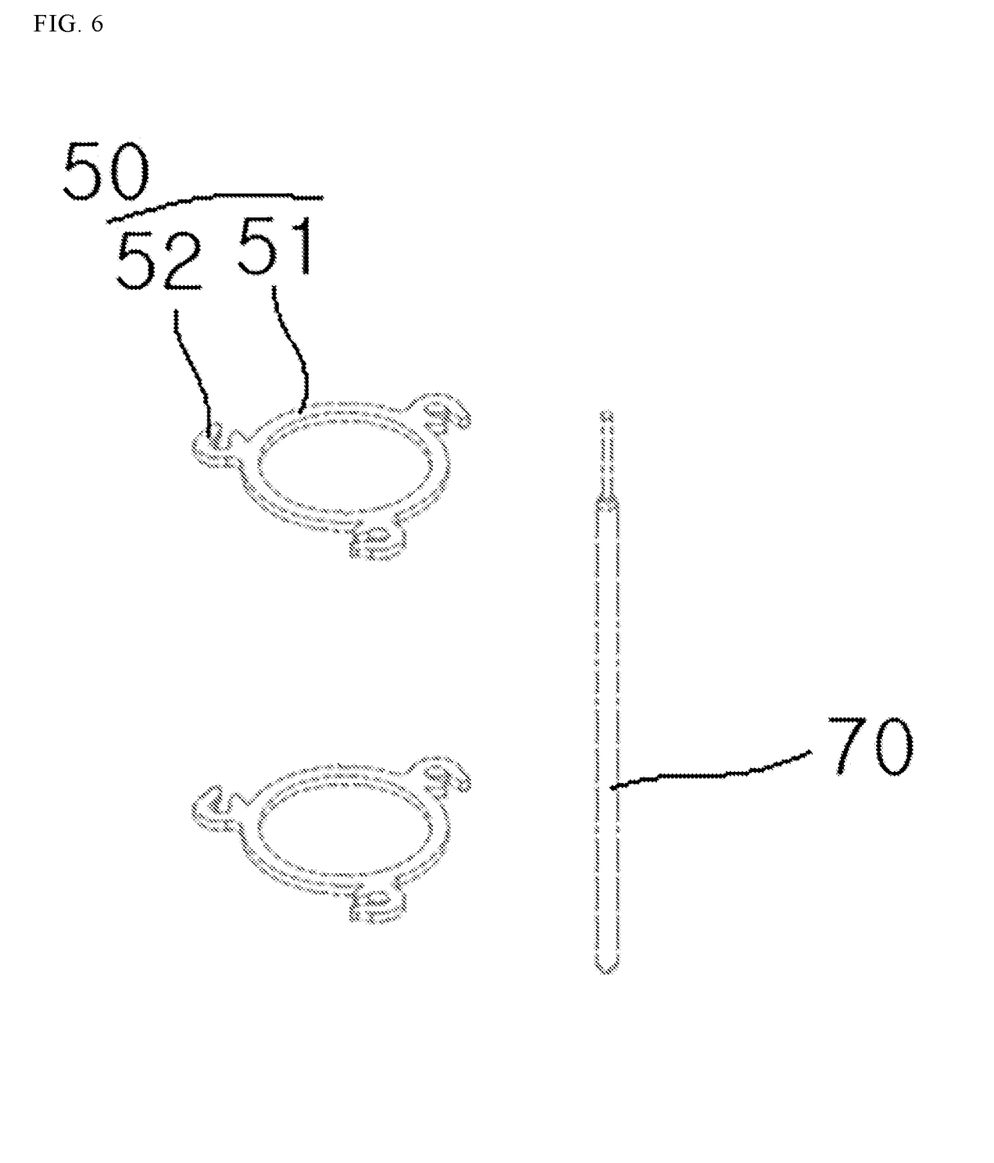
FIG. 6 is an exploded perspective view of FIG. 5.

To this end, the water sampler of one embodiment of the present disclosure may further include a thermometer 70 installed in the first accommodation portion 13, and two or more holders 50 may be vertically spaced apart from each other around the glass bottle so as to install the thermometer 70 in the first accommodation portion 13. On the other hand, in an embodiment of the present disclosure, it is illustrated that two holders 50 are spaced part from each other along the vertical direction of the glass bottle, but the present disclosure is not limited thereto, and the total number of holders installed in the glass bottle 20 may be three or more as necessary.

Referring additionally to FIGS. 5 and 6, the holder 50 may include a holder body 51 and a ring portion 52 for inserting and fixing the thermometer 70.

The holder body 51 is formed in a band shape to surround the circumference of the glass bottle 20, and the ring portion 52 is a portion formed to protrude in a ring shape externally from an outer surface of the holder body 51 such that the thermometer 70 is inserted and fixed. In this case, the size of the ring portion 52 may be adjusted such that an edge of the ring portion 52 is in close contact with an inner surface of the first wall 12 of the container 10, and when the edge of the ring portion 52 is in close contact with an inner surface of the first wall 12 of the container 10, the position in which the holder body 51 is installed may be kept more stable and the measured temperature accuracy of the sample can be further improved.

According to such a structure, the thermometer 70 is supported by the ring portion 52 of the holder 50 and installed vertically in the first accommodation portion 13 provided between the container 10 and the glass bottle 20.

Figure 7:
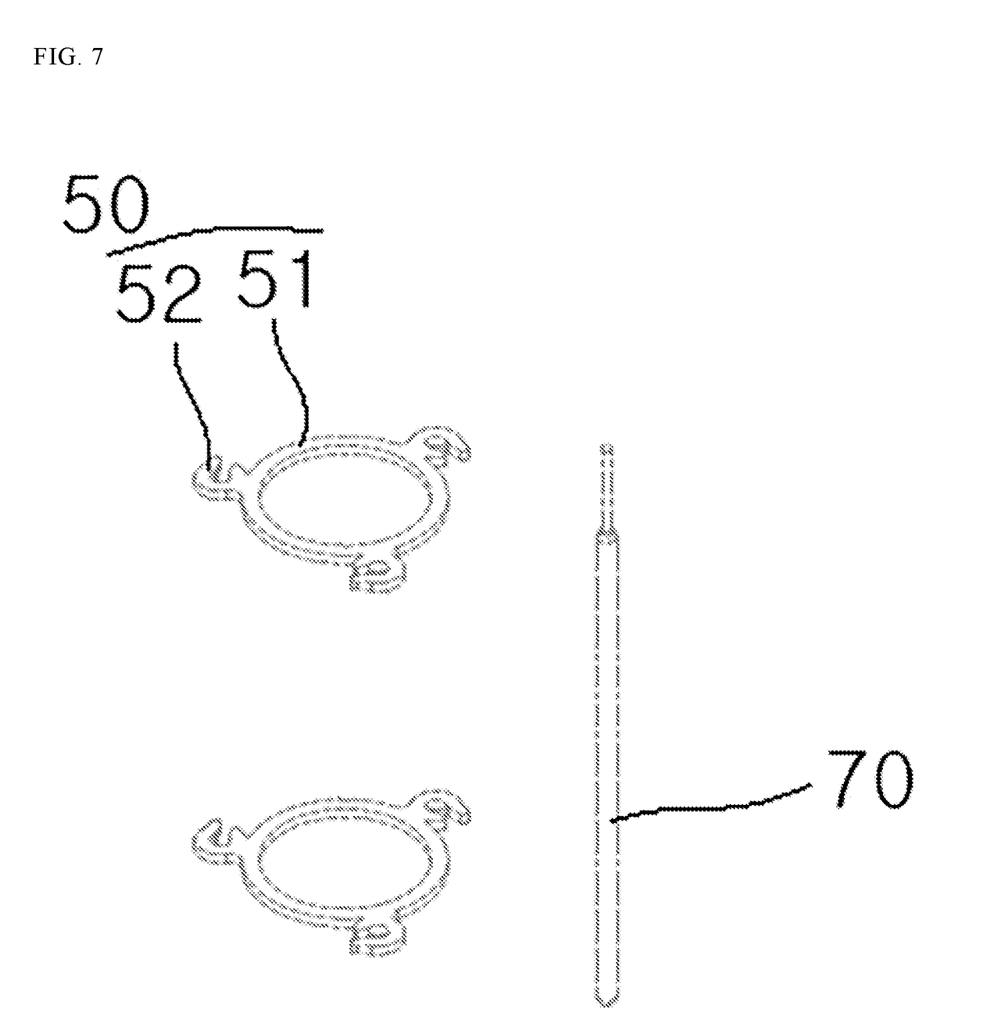
FIG. 7 is a perspective view illustrating a state in which the holder and the thermometer are coupled in the water sampler according to another embodiment of the present disclosure.

In contrast, as illustrated in FIG. 7, the holder body 51 of each of the upper and lower holders 50 may be provided with one or more through holes 53, and a full thread bolt 54 having a thread formed therein may be inserted into the through hole 53 such that the full thread bolt 54 vertically penetrates the though hole 53, and fixing nuts 55 may be fastened to upper and lower surfaces of the through-hole 53 into which the full thread bolt 54 is inserted.

When the thermometer 70 installed in this way is used, the temperature of the sample may be measured immediately from time to time in a situation where the temperature increases rapidly after collecting the sample. Therefore, efficient response is possible immediately depending on the situations at the sampling site, such as measuring a characteristic value of the sample simultaneously with collecting the sample.

For example, according to the Ministry of Environment Notice (No. 2004-188) on the water pollution process test method, hydrogen ion concentration or dissolved oxygen (electrode method) has to be measured immediately with temperature, samples collected for BOD or COD measurements needs to be maintained at 4° C. or lower, and when the temperature of the collected sample exceeds 4° C., the BOD and COD of the sample has to be measured immediately before cooling or exceeding a corresponding temperature at the site. In one embodiment of the present disclose, when using the thermometer 70 installed in the first accommodating portion 13, such determination may be easily carried out right away.

In addition, if necessary, a plurality of ring portions 52 may be formed at predetermined intervals along the circumference of the holder body 51. When the plurality of ring portion 52 are formed along the circumference of the holder body 51, a plurality of thermometers 70 may be installed, and when the plurality of thermometers 70 are installed, the temperature of the thermometer 70 may be easily checked at various angles from the outside of the container 10. When the collected sample is very cloudy, the whole water sampler is tilted to one side such that one thermometer 70 is exposed outside the sample, and then, the temperature of the thermometer 70 exposed outside the sample may be checked. In this case, some of the collected water may be discharged externally for the purpose of the exposure of the thermometer 70 as necessary.

Meanwhile, the holder body 51 of the holder 50 and the ring portion 52 may be made of a thermally conductive metal so as to accurately measure the temperature of the collected sample in real time. Accordingly, it is possible to accurately measure the average temperature value of the sample collected in the first accommodation portion 13 of the container 10 made of plastic and the sample collected in the second accommodation portion 21 of the glass bottle 20.

Specifically, if the edge of the ring portion 52 is formed to come into close contact with the inner surface of the first wall 12 of the container 10, when the holder body 51 and the ring portion 52 are formed of a thermally conductive metal, not only the temperature of the sample accommodated in the first accommodation portion 13 but also the temperature of the sample accommodated in the second accommodation portion 21 may be reflected as necessary.

As another example of using the water sampler of one embodiment of the present disclosure, there is a degree management field evaluation. In accordance with ES 04130.1 which is the water pollution test standard, the composition of the sample must not change until the sample arrives in the laboratory, and BOD samples needs to be stored in a dark place at 4° C. after collection and may be stored for up to 48 hours for testing, and is recommended to be tested within 6 hours as much as possible.

In addition, when there is a risk of contamination or deterioration while transporting samples, on-site samples or transport-based samples are prepared, and the samples are tested in the same way to check for contamination. Furthermore, in order to perform BOD and COD measurements, a pretreatment of the samples is required as follows.

The pretreatment of a BOD test complies with ES 04305.1. When collecting a sample for testing, the sample are sufficiently shaken and mixed for homogenizing. For an acidic or alkaline sample whose pH deviates from the range of 6.5 to 8.5, the sample is neutralized with a hydrochloric acid solution (1 M) or a sodium hydroxide solution (1 M) to adjust the pH to pH 7 to 7.2. In this case, when dissolved oxygen is supersaturated at a water temperature of 20° C. or less, after raising the water temperature to 23° C. to 25° C., the sample is ventilated and left for 15 minutes and then cooled, and the water temperature is set to 20° C. again. In addition, after collecting the BOD sample, the sample needs to be stored in the dark place at 4° C. and may be stored for up to 48 hours for testing, and is recommended to be tested within 6 hours as much as possible.

As described above, according to the evaluation method and characteristics of the sample, it is necessary to accurately measure the temperature of the sample and adjust the water temperature, and in the embodiment, since the thermometer is provided inside the water sampler, not outside the water sampler, it is possible to easily and accurately measure the temperature of the sample in real time without being affected by the outside temperature.

The scope of the present disclosure is not limited to the above-described embodiments and the accompanying drawings but is defined by the appended claims. Those of ordinary skill in the art may make various replacements, modifications, or changes without departing from the scope of the present disclosure defined by the appended claims, and these replacements, modifications, or changes should be construed as being included in the scope of the present disclosure.

EXPLANATION OF SIGNS

10: container
11: bottom plate
12: wall surface
13: first accommodation portion
14: weight
15: bottleneck
20: glass bottle
30: second stopper
31: second upper plate
32: second wall part
33: rod-shaped handle
35: elastic member
40: first stopper
41: first upper plate
42: first wall
43: sample inlet
50: holders
70: thermometer
80: fixing member

The invention claimed is:

1. A water sampler, comprising:
a container which is open at the top thereof;
a first stopper which comprises a first upper plate having a through hole formed therein, and a first wall which extends downwardly from an edge of the first upper plate and of which an upper end is coupled to an outer surface of a bottleneck of the container, wherein at least one sample inlet is formed on a side surface of the first wall;
a second stopper which comprises a second upper plate having a handle portion long protruding upwardly to be exposed through the through hole of the first stopper and connected to a first rope, and a second wall extending downwardly from an edge of the second upper plate, wherein the second stopper is installed to move up and down in the first stopper such that the second wall selectively opens or closes an open upper portion of the container;
an elastic member which is disposed between the first upper plate and the second upper plate;
a weight which is disposed in the bottom of the container; and
a fixing member which fixes the weight to the container and to which a second rope is connected.

2. The water sampler of claim 1, wherein the container further comprises a transparent glass bottle which is made of transparent plastic and is open at the top thereof by containing a bottom plate and a wall surface and a first accommodation portion is provided inside, and in which the first stopper is coupled to an upper end of the wall surface,
wherein the transparent glass bottle is installed on the bottom plate of the container to be spaced apart from the wall surface of the container such that a second accommodation portion is provided inside, and an upper end of the transparent glass bottle is disposed higher than the bottleneck of the container such that a sample collected in the second accommodation portion is not mixed with a sample collected in the first accommodation portion when the sample is drained.

3. The water sampler of claim 2, wherein a mounting protrusion is provided on the bottom plate of the container such that an upper end of the glass bottle can be inserted and fixed.

4. The water sampler of claim 2, wherein two or more holders are installed around the glass bottle to be spaced apart in a vertical direction,
wherein the holder comprises: a band-shaped holder body surrounding a circumference of the glass bottle; and a ring portion protruding from the holder body, and the water sampler further comprises a thermometer supported by the ring portion disposed vertically and installed in the first accommodating portion provided between the container and the glass bottle.

5. The water sampler of claim 4, wherein the holder is made of a thermally conductive metal.

\* \* \* \* \*